United States Patent [19]

Hayama et al.

[11] Patent Number: 5,480,634
[45] Date of Patent: Jan. 2, 1996

[54] HAIR-CARE PRODUCTS CONTAINING COPOLYMERS FORMED FROM UNSATURATED HYDROPHILIC MONOMERS AND UNSATURATED MONOMERS HAVING A POLYSILOXANE GROUP

[75] Inventors: Kazuhide Hayama; Kanji Narazaki; Sigeoki Kawaguchi, all of Yokkaichi, Japan

[73] Assignee: Mitsubishi Chemical Corporation, Tokyo, Japan

[21] Appl. No.: 170,447

[22] Filed: Dec. 2, 1993

Related U.S. Application Data

[60] Continuation of Ser. No. 935,032, Aug. 25, 1992, abandoned, which is a division of Ser. No. 549,485, Jul. 6, 1990, Pat. No. 5,166,276.

[30] Foreign Application Priority Data

Jul. 12, 1989 [JP] Japan ................................ 1-179811

[51] Int. Cl.$^6$ .................................................. A61K 7/075
[52] U.S. Cl. ............................................................ 424/70.12
[58] Field of Search ............................ 424/70, 71, 70.12

[56] References Cited

U.S. PATENT DOCUMENTS

| 3,208,911 | 8/1965 | Oppliger et al. ............................ 424/70 |
| 4,584,337 | 4/1986 | Lee et al. .................................... 524/500 |
| 4,902,499 | 2/1990 | Balish, Jr. et al. ......................... 424/47 |
| 5,051,486 | 9/1991 | Kuroda et al. ............................. 526/279 |
| 5,061,481 | 10/1991 | Suzuki et al. ............................ 526/279 |
| 5,087,443 | 2/1992 | Chizat et al. ............................... 424/47 |
| 5,166,276 | 11/1992 | Hayama et al. .......................... 526/279 |
| 5,275,809 | 1/1994 | Chen et al. ................................ 424/70 |

FOREIGN PATENT DOCUMENTS

| 2218351 | 9/1974 | France ........................................ 526/279 |
| 63291925 | 11/1988 | Japan ......................................... 526/279 |
| 1250305 | 10/1989 | Japan . |
| 264117 | 3/1990 | Japan ......................................... 526/279 |
| 362810 | 3/1991 | Japan ......................................... 526/279 |
| 4161459 | 6/1992 | Japan ......................................... 524/266 |
| 4359913 | 12/1992 | Japan ......................................... 526/279 |
| WO8400968 | 3/1984 | WIPO ......................................... 526/279 |

OTHER PUBLICATIONS

Todd et al American Perfumer and Cosmetics, Tat. 71.

*Primary Examiner*—Peter F. Kulkosky
*Attorney, Agent, or Firm*—Koda and Androlia

[57] ABSTRACT

A polymer suitable for use in hair care products comprising a copolymer comprising (a) a unit of a hydrophilic ethylenically unsaturated monomer such as dimethylaminoethyl methacrylate in a quantity of 15 to 99.9% by weight;

(b) a unit of an ethylenically unsaturated monomer having a polysiloxane group such as:

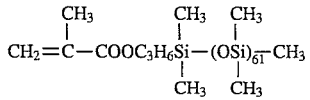

in a quantity of 0.1 to 85% by weight; and (c) a unit of an optional hydrophobic unsaturated monomer such as lauryl methacrylate in a quantity of 0 to 84.9% by weight.

7 Claims, No Drawings

HAIR-CARE PRODUCTS CONTAINING COPOLYMERS FORMED FROM UNSATURATED HYDROPHILIC MONOMERS AND UNSATURATED MONOMERS HAVING A POLYSILOXANE GROUP

This is a continuation of application Ser. No. 07/935,032, filed Aug. 25, 1992, now abandoned, which is a division of application Ser. No. 549,485, filed Jul. 6, 1990, now U.S. Pat. No. 5,166,276.

BACKGROUND OF THE INVENTION

1. Field of the Art

The present invention relates to novel polymers suitable for use in hair-care products. More particularly, the present invention relates to a polymer comprising as an essential constituent units of a hydrophilic unsaturated monomer which affords hair an excellent brilliance and gloss and a smooth feeling and has an excellent washability, and into which a polysiloxane group has been introduced.

The polymers in accordance with the present invention can be used for providing hair with settability, softness, gloss, smooth feeling, smooth combing, recovery from damages, manageability and the like.

2. Related Art

In hair-care products such as a shampoo, a rinse, a hair treatment product, a hair setting product or a cold permanent wave solution have heretofore been used oily components such as silicone compounds, ester compounds, hydrocarbon compounds or the like in an emulsified, solubilized or dissolved state, for the purpose of providing hair with brilliance, gloss and smoothness. The silicone type compounds among them have these years been used extensively because of their excellent. properties.

Specifical examples of application of silicone compounds include (i) hair-care products into which silicone oils such as polydimethylsiloxane, polymethlyphenylsiloxane or the like and their emulsion have been incorporated; (ii) aerosol foam type hair setting products such that an etherified silicone such a polydimethylsiloxane-polyoxyalkylene block copolymer or the like has been incorporated into a hair-fixative polymer such as a cationic polymer or an amphoteric polymer to form, together with a propellant, the aerosol products (Japanese Patent Laid-Open Publication No. 135319/88); (iii) shampoos and rinses into which an aminated organopolysiloxane emulsion has been incorporated (Japanese Patent Laid-Open Publication No. 307811/63); (iv) hair conditioning product and hair-setting products such that an aminated organopolysiloxane emulsion has been incorporated into a cationic polymer compound and an amphoteric polymer compound, respectively, to form the hair conditioning product and hair-setting products (Japanese Patent Laid-Open Publication No. 275515/88); and (v) hair-care products in which polydimethylsiloxane or polymethylphenylsiloxane having a high molecular weight is used (Japanese Patent Laid-Open Publication No. 243019/88).

However, the silicone oils or the etherified silicones when used may cause problems such as giving sticky feeling to hair or undergoing reverse transition of silicone from hair to hand or clothing if they are formulated in a large amount or if the product is used repeatedly for a long time. Emulsions of silicones may have problems in dispersion stability. Silicones having a high molecular weight may have problems in the compatibility with hair care resins or additives, so that they have restrictions in formulation whereby their applicability in a variety of hair-care products is restricted.

The silicone compounds having no such hydrophilic groups as a polyether group are difficult to be removed by usual hair washing, and thus when consumers use the products into which the less hydrophilic silicone compounds have been formulated for a long period repeatedly, hair tends to be hydrophobic and causes problems in hair dyeing or permanent waving.

SUMMARY OF THE INVENTION

The object of the present invention is to solve the aforementioned problems and to provide a novel polymer for hair-care products which provides hair with an excellent gloss and brilliance and a smooth feeling without stickiness and will not be accumulated in the hair and cause no problems for being formulated into cosmetics.

The polymer suitable for use in hair-care products according to the present invention comprises a copolymer comprising (a) a unit of a hydrophilic ethylenically unsaturated monomer in a quantity of 15 to 99.9% by weight; (b) a unit of an ethylenically unsaturated monomer having a polysiloxane group in a quantity of 0.1 to 85% by weight; and (c) a unit of a hydrophobic ethylenically unsaturated monomer in a quantity of 0 to 84.9% by weight.

In the present invention, an ethylenically unsaturated monomer having a polysiloxane group (b) is copolymerized with a hydrophilic ethylenically, unsaturated monomer (a) and, if necessary, with a hydrophobic ethylenically unsaturated monomer (c), so that the defects in conventional silicone compounds such as generation of the sticky feeling of hair or the reverse transition of silicone encountered when the silicone compounds,are formulated in a large quantity or on the use for a long period repeatedly can be solved thanks primarily to the use of the compound (b), and the silicone can be easily removed by washing hair thanks primarily to the component (a). Further, a hydrophilic ethylenically unsaturated monomer component (a) and a hydrophobic ethylenically unsaturated monomer component (c) are appropriately chosen in terms of their types and relative proportions, so that the polymer can now be incorporated into hair care products without restriction.

DESCRIPTION OF THE PREFERRED EMBODIMENT OF THE INVENTION

[I] Polymer

Unsaturated Monomer

The polymer suitable for use in the present invention is obtained by copolymerizing two essential namely (a) a hydrophilic unsaturated monomer and (b) an unsaturated monomer having a polysiloxane group, and an optional monomer, namely ( c ) hydrophobic unsaturated monomer. Each of these monomers of the categories (a) , (b) and (c) can be used in admixture within respective categories. Hydrophilic unsaturated monomers (a):

Preferably , the hydrophilic unsaturated monomer as the component ( a) are hydrophilic unsaturated monomers of a cationic, an ionic, nonionic or amphoteric nature and polymerizable through radical polymerization mechanism. It is preferable that they have a solubility in water in a range of 10 g/100 g of water or more (25° C.).

Examples of the cationic unsaturated monomers include (i) monomers derived from acrylic acid or methacrylic acid, which is referred to hereinafter collectively as (meth)acrylic acid, and a quaternarized epihalohydrin product of a trialkylamine having 1 to 4 carbon atoms in the alkyl such as (meth)acryloyloxyhydroxypropyltrimethylammonium chloride and (meth)acryloyloxyhydroxypropyltriethylammonium bromide;

(ii) amine derivatives of (meth)acrylic acid or amine derivatives of (meth)acrylamide derived from (meth)acrylic acid or (meth)acrylamide and a dialkylalkanolamine having $C_1$ to $C_4$ alkyl groups such as dimethylaminoethyl (meth)acrylate, diethylaminoethyl (meth)acrylate, dimethylaminopropyl (meth)acrylate, or dimethylaminopropyl (meth)acrylamide; and (iii) derivatives of the product's of the group (ii) above by (1) neutralization with an acid such as hydrochloric acid, or lactic acid, (2) denaturation with a halogenated alkyl such as methyl chloride, ethyl chloride, methyl bromide, or ethyl iodide, (3) denaturation with a halogenated fatty acid ester such as ethyl monochloroacetate, or methyl monochloropropionate, and (4) denaturation with a dialkyl sulfate such as dimethyl sulfate, or diethyl sulfate.

Furthermore, the cationic unsaturated diallyldimethylammonium chloride and the like.

These cationic unsaturated monomers can be copolymerized in the form as such, or as an alternative they can be copolymerized in the form of their precursors, which are then cationized by a so-called cationizing agent. More particularly, dimethylaminoethyl (meth)acrylate is copolymerized, and the copolymer obtained will then be cationized by a quaternizing agent such as hydrochloric acid, ethyl monochloroacetate, dimethyl sulfate or the like to form a desired copolymer of the cationic unsaturated monomer.

Examples of the anionic unsaturated monomers include:

(i) unsaturated carboxylic acid monomers such as (meth) acrylic acid, maleic acid, .maleic anhydride, itaconic acid, fumaric acid, and crotonic acid;

(ii) half esters of an unsaturated polybasic acid anhydride such as succinic anhydride, phthalic anhydride or the like with a hydroxyl group-containing (meth)acrylates such as hydroxyethyl (meth)acrylate, hydroxypropyl (meth)acrylate or the like, (iii) monomers having a sulfonic acid group such as styrenesulfonic acid, sulfoethyl (meth)acrylate or the like, and (iv) monomers having a phosphoric acid group such as acid phosphooxyethyl (meth)acrylate, 3-chloro-2-acid phosphooxypropyl (meth)acrylate or the like.

These anionic unsaturated monomers can be used in the form of an acid or after partial or complete neutralization, or they can be copolymerized in the form of acid and then neutralized partially or completely. Examples of the bases used for neutralization include alkali metal hydroxides such as lithium hydroxide, potassium hydroxide, sodium hydroxide or the like, aqueous ammonia, amine compounds such as mono-, di- or triethanolamine, triethylamine, morpholine, aminomethylpropanol, aminoethylpropanediol or the like.

Examples of the nonionic unsaturated monomers include monomers derived from (meth)acrylic acid or (meth)acrylamide and an alkylene oxide having 2 to 4 carbon atoms such as hydroxyethyl (meth)acrylate, polyethyleneglycol mono(meth)acrylate, methoxypolyethyleneglycol mono(meth)acrylate, methoxypoly(ethylene glycol/propylene glycol) mono(meth)acrylate, polyethylene glycol di(meth)acrylate, N-polyalkylenoxy(meth)acrylamide or the like; acrylamide, N-vinylpyrrolidone or the like.

Examples of the amphoteric monomers include zwitter ionized derivatives of the aforementioned amine derivatives of (meth)acrylic acids or the amine derivatives of (meth)acrylamide such as dimethylaminoethyl (meth)acrylate, dimethylaminopropyl-(meth)acrylamide by a halogenated fatty acid salt such as potassium monochloroacetate, sodium monobromopropionate, aminomethylpropanol salt of monochloroacetic acid, triethanolamine salt of monochloroacetic acid and the like; and modified products with propanesultone of the aforementioned amine derivatives of (meth)acrylic acid or (meth)acrylamide.

These amphoteric unsaturated monomers, like the aforementioned cationic unsaturated monomers, can be copolymerized in the form as such or as an alternative they can also be copolymerized in the form of their precursors, which are then converted into amphoteric state. It is also possible to remove the salt produced as a by-product of amphoterization by filtration or ion-exchange, if necessary, before copolymerization step or after the copolymerization-amphoterization step. These technologies is described in detail in Japanese Patent Laid-Open Publication No. 92809/81.

The hydrophilic unsaturated monomer is used in an amount of 15 to 99.9% by weight per weight of total monomers. If the amount is less than 15% by weight, the copolymer thus obtained has problems that it is hardly soluble in water and/or an ethanolic solvent or it is difficult to be removed upon hair washing, The amount of the monomer can be selected at will according to the uses with the upper limit of 99.9% by weight. In other words, the hydrophilic unsaturated monomer is preferably used in an amount of 15 to 59.5% by weight when the polymer is used as a hair-setting polymer and 30 to 99.5% by weight when the polymer is used as a hair-conditioning polymer. Polysiloxane group containing unsaturated monomer (b):

The polysiloxane group-containing unsaturated monomer as the component (b) is a monomer which has at least one unsaturated group having radical polymerizability and a polysiloxane group

wherein a=1 to 150.

Specifically, compound represented by the following formula (I) are mentioned:

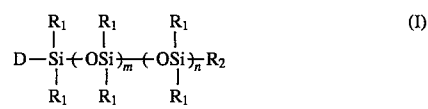

wherein D, $R_1$, $R_2$, m and n have the following meanings, respectively:

D=an unsaturated group having radical polymerizability such as a vinyl group, a vinylalkylene group, a vinylhydroxyalkylene group, an acryloyloxyalkylene group or a methacryloyloxyalkylene group;

$R_1$=a hydrogen atom, a phenyl group, an alkyl group having 1 to 10 carbon atoms, a polyoxyalkylene group, a polyoxyalkylene group of which end has been substituted by an ether or ester group, a polyalkylenepolyamine group, a fatty acid group or a polysiloxane group, respectively;

$R_2$=a hydrogen atom, a phenyl group, an alkyl group having 1 to 10 carbon atoms, a polyoxyalkylene group, a polyoxyalkylene group of which end has been substituted by an ether or ester group, a polyalkylenepolyamine group, a fatty acid group or a polysiloxane group, or an unsaturated group having radical polymerizability such as a vinyl group, a vinylalkylene group, a vinylhydroxyalkylene group, an acryloyloxyalkylene group or a methacryloyloxyalkylene group;

m=an integer from 4 to 150; and n=an integer from 0 to 150, wherein the sum of m and n is within 150.

In the above-described formula (I), the sum of m and n is preferably in the range of 4 to 150. If the sum is less than 4, the polymer obtained by the copolymerization cannot exhibit the advantages inherent in the silicone compound. If the sum exceeds 150, the copolymerizability with the unsaturated monomers of the components (a) and (b) is undesirably lowered.

Embodiments of the unsaturated monomer having a polysiloxane group include the unsaturated monomers illustrated by the following formulae (II)–(IV):

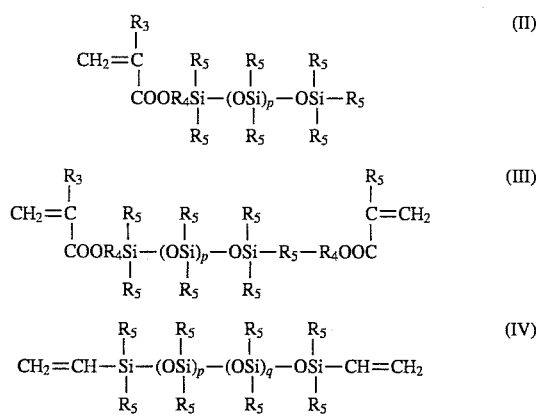

wherein $R_3$–$R_6$, p and q have the following meanings independently of each other between the formulae:

$R_3$=a hydrogen atom or a methyl group;

$R_4$=an alkylene group having 1 to 4 carbon atoms;

$R_5$=an alkyl group having 1 to 10 carbon atoms or a phenyl group;

p=an integer of 1 or more; and q=an integer of 1 or more, wherein the sum of p and q are within 150.

The unsaturated monomers illustrated by the general formula (II) can be obtained as commercially available products (manufactured by Chisso Corporation) such as FM0711 (trade name; p=10, $R_3$=a methyl group, $R_4$=a propylene group, and $R_5$=a methyl group in the aforementioned formula (II); referred to as polysiloxane FM0711 in the preparation example below), FM0721 (p=60, $R_3$=a methyl group, $R_4$=a propylene group, and $R_5$=a methyl group in the aforementioned formula (II); referred to as polysiloxane FM0721 in the preparation example below) and FM0725 (p=130, $R_3$=a methyl group, $R_4$=a propylene group, and $R_5$=a methyl group in the aforementioned formula (II); referred to as polysiloxane FM0725 in the preparation example below).

The monomers illustrated by the general formula (III) can be easily obtained by the reaction of a polysiloxane having both ends of silanol and a (meth)acryloyloxyalkylene (having 1 to 4 carbon atoms) di(alkyl (having 1 to 4 carbon atoms) or phenyl) halosilane.

The unsaturated monomers illustrated by the general formula (IV) can be obtained as commercially available products (manufactured by Chisso Corporation) such as FP2231 (trade name; p=30, q=5, $R_5$=a methyl group and $R_6$=a phenyl group; referred to as polysiloxane FP2231 in the preparation example below), FP2241 and FP2242.

The polysiloxane group-containing unsaturated monomers illustrated by the general formulae (II)–(IV) can be copolymerized in the form as such. Alternatively, they can be copolymerized in the form of their precursor and a polysiloxane group will then be added. Specifically, a polysiloxane group can be introduced by copolymerizing the monomer in the form of (meth)acrylic acid and then reacting with a polysiloxane having a terminal epoxy group (for example, a compound illustrated by the following structural formula (1), this compound being referred to as polysiloxane FM0521 in the preparation example below). A polysiloxane group can also be introduced by polymerizing the monomer in the form of (meth)acryloyloxyalkylenedialkylchlorosilane and then reacting with a polysiloxane having a terminal epoxy group or a polysiloxane having a terminal modified with an amino group. Structural formula (1):

Structural formula (1):

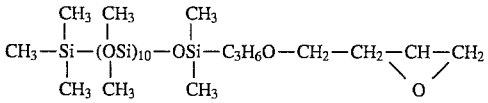

The quantity of copolymerization of the polysiloxane group containing unsaturated monomer (b) is in the range of 0.1 to 85% by weight, preferably 0.5 to 70% by weight, more preferably 0.5 to 20% by weight, of the total monomer weight. If the amount is less than 0.1% by weight, the copolymer obtained cannot afford hair an excellent gloss and brilliance or a smooth feeling. If the amount of the monomer exceeds 85% by weight, it will cause problems when it is incorporated into cosmetics or when it is used repeatedly over a long period.

If the monomer represented by the formula (I) described above is monofunctional and the sum of m and n is 80 or more, the copolymerizability of the monomer decreases, so that it is effective to use a bifunctional monomer wherein $R_2$ is a vinyl group, an acryloyloxy group or a methacryloyloxy group in combination with the monofunctional monomer.

Hydrophobic unsaturated monomer (c):

The hydrophobic unsaturated monomer of the component (c) is a hydrophobic unsaturated monomer having radical polymerizability which is used, if necessary, in order to afford the copolymer obtained a hydrophobic property and the strength, hardness and softness of film derived therefrom. The hydrophobic unsaturated monomer has preferably a solubility in water in the range of less than 10 g/100 g in water (25° C.).

Examples of the hydrophobic unsaturated monomers include, for example, (a) saturated and unsaturated alkyl (meth)acrylates having 1 to 24 carbon atoms in the alkyl such as methyl (meth)acrylate, allyl (meth)acrylate, isobutyl (meth)acrylate, cyclohexyl (meth)acrylate, octyl (meth)acrylate, lauryl (meth)acrylate, oleyl (meth)acrylate, behenyl (meth)acrylate and the like; (b) hydrophobic (meth)acrylates and their derivatives such as butoxyethyl (meth)acrylate, benzyl (meth)acrylate, tetrahydrofurfuryl (meth)acrylate, ethyleneglycol di(meth)acrylate, 1,3-butyleneglycol di(meth)acrylate, diacetonacrylamide and the like; (c) aromatic unsaturated monomers such as styrene, chlorostyrene, vinyltoluene and the like; and (d) vinyl esters such as vinyl acetate and the like.

The amount of the hydrophobic unsaturated monomer polymerized is in the range of 0 to 84.9% by weight to the total monomer weight, and this monomer is not an essential component. If the amount of this monomer exceeds 84.9% by weight, the copolymer thus obtained may have problems that it becomes hardly soluble in water and/or an ethanolic solvent or it is difficult to be removed from hair upon hair washing. The amount of the monomer can be selected at will according to the uses with the upper limit of 84.9% by weight. The hydrophilic unsaturated monomer is preferably used in an amount of 40 to 84.5% by weight when the polymer is used as a hair-setting polymer and 0 to 69.5% by weight when the polymer is used as a hair-conditioning polymer.

When a bifunctional unsaturated monomer such as ethyleneglycol di(meth)acrylate, allyl (meth)acrylate or the like is used, it is preferably used in an amount of 2% by weight or less to the total monomer weight.

Formation of copolymer

The unsaturated monomers can be copolymerized by well-known radical polymerization methods such as bulk polymerization, solution polymerization, suspension polymerization, emulsion polymerization or the like.

Preferred polymerization method is a solution polymerization method, which is conducted by a process comprising dissolving monomers in a solvent, adding a polymerization initiator and stirring under heating the mixture under the nitrogen stream.

The solvent is preferably water and an alcohol such as methanol, ethanol, isopropanol, ethyleneglycol and butylcellosolve. These solvents can be used in combination. The polymerization initiator is preferably a peroxide such as benzoyl peroxide, lauroyl peroxide and an azo compound such as azobisisobutyronitrile or the like.

The monomers concerned are usually used in such a way that all of them in types and amounts are added to the polymerization at once from the initiation of polymerization, but alternatively they can be used in such a way that some of them in types and/or amounts are added to polymerization separately. The solvent is preferably used in such an amount that the copolymer solution obtained has a polymer concentration of 10 to 65% by weight. The amount of the monomers charged may be determined in consideration of factors such as the copolymerizability or the conversion so that the copolymer obtained has a predetermined composition. It goes without saying that the monomers charged has the same composition as that of the copolymer in the case of the conversion of 100%.

The molecular weight of the copolymer can be decided at will by appropriately selecting the polymerization conditions such as polymerization temperature, the kinds and amounts of polymerization initiators, addition methods, the amounts of solvent used, the chain transfer agents when used or the like. In general, the copolymers obtained have preferably the molecular weight in the range of 1,000 to 500,000.

The copolymer can be obtained as a solid by removing the solvent from a copolymer solution, or the solid thus obtained can be diluted with any solvents to obtain a copolymer solution, which are used for further applications. The copolymers thus obtained and the solutions may be used in admixture of the two or more.

[II] Use of the polymer/hair-care products

The copolymer thus obtained is preferably used as a polymer suitable for hair-care products in an amount of 0.1 to 10% by weight in well-known compositions such as shampoos, rinses, hair treatment products, hair setting products, cold permanent wave lotions or the like. The hair-care products into which the copolymer is incorporated may be of any forms such as liquid, cream, emulsion, gel or the like. It may also be used in combination with well-known conventional naturally occurring polymers, modified products of naturally occurring polymers or synthetic polymers.

Hair-care products in which the copolymer in accordance with the present invention is used include hair setting compositions for setting hair in desired hair style such as aerosol hair sprays, pump hair sprays, foaming type hair sprayss, hair mists, hair setting lotions, hair styling gels, hair liquids, hair creams, hair oils and the like, and those for providing hair with softness, gloss, smooth combing, recovery from damage, manageability and the like such as shampoos, rinses, hair treatment lotions, cold permanent wave lotions and the like.

More particularly, typical examples of hair-care products in which the copolymers in accordance with the present invention are incorporated are as follows.

(1) Hair-care products for hair setting:

Hair-care products for hair setting include those in which water and/or an alcohol e.g. ethanol or isoporpanol is used as a solvent known in the art such as aerosol hair spray, pump hair spray, foaming type hair spray, hair mist, hair-setting lotion, hair-styling gel, hair liquid, hair cream, hair oil and the like.

The copolymers in accordance with the present invention are used in these hair-care products as a partical or total substitute for or in combination with anionic, nonionic, cationic and amphoteric polymers and polysiloxne polymers conventionally used in these hair-care products.

The copolymers in accordance with the present invention can also be used in hair-care products in combination with oils or fats, humectants, solubilizing agents, emulsifiers, thickeners, germicides, perfumes and the like conventionally used in hair-care products.

For these uses, it is preferable that the copolymer comprises a unit of the hydrophilic monomer (a) in 15 to 59.5% by weight, a unit of the monomer comprising a polysiloxane group (b) in 0.5 to 45% by weight, and a unit of the hydrophobic monomer (c) in 40 to 84.5% by weight.

When the ionic natures of the hydrophilic monomer (a) are nonionic, anionic, amphoteric in that the monomer has cationic and anionic natures in its molecule, or amphoteric in that a cationic monomer and an anionic monomer are in admixture, it is preferable that a unit of the copolymer comprises the hydrophilic monomer (a) in 20 to 59.5% by weight, a unit of the monomer comprising a polysiloxane group (b) in 0.5 to 40% by weight, and a unit of the hydrophobic monomer (c) in 40 to 79.5% by weight.

When the hydrophilic monomer (a) is cationic, it is preferable that the copolymer comprises a unit of the hydrophilic monomer (a) in 15 to 54.5% by weight, a unit of the monomer comprising a poly siloxane group (b) in 0.5 to 45% by weight, and a unit of the hydrophobic monomer (c) in 40 to 84.5% by weight.

When the hydrophilic monomer (a) is amphoteric in that a cationic monomer and an anionic monomer are in admixture, the ratio by weight of cationic monomer units/anionic monomer units is preferably 1/9 to 9/1.

(2) Hair-care products for hair conditioning: Hair-care products for hair conditioning include those in which water and/or an alcohol, e.g. ethanol or isopropanol is used as a solvent such as shampoos, hair rinses, cold permanent wave lotions and the like and those in which water and/or an alcohol e.g. ethanol or isopropanol, or an alcohol and/or a hydrocarbon of a boiling point of 50° to 300° C. such as hair treatment products.

When the hair-care products are shampoos in which the copolymers in accordance with the present invention are used, it is a conventional practice to use in the shampoos anionic, amphoteric or nonionic surfactants, and it is also possible to use in the shampoos foam improves, thickeners, hydrotropes, emulsifiers, conditioning aids, germicides, perfumes and the like.

When the hair-care products are hair-rinses in which the copolymers-in accordance with the present invention are used, it is a conventional practice to use in the rinses cationic surfactants, and it is also possible to use in the rinses oils and facts, cationic surfactants, amphoteric surfactants, humectants, solubilizing agents, emulsifiers, thickeners, germicides, hair tonics, perfumes and the like.

When the hair care products are cold permanent wave lotions, it is a conventional practice to use in the lotions bromates, perborates, oxidation-reduction compositions e.g. thioglycolates or cysteine and the like. It is also possible to use in the lotion surfactants, thickeners, stabilizing agents, emulsifiers, conditioning aids, humectants, germicides, perfumes and the like.

When the hair-care products are hair treatment products, the copolymers in accordance with the present invention are used in these hair treatment products as a partial or total substitute for or in combination with cationic surfactants and/or cationic polymers e.g. cationic polypeptides, cationic celluloses, cationic polysiloxanes and the like. It is also possible to use in the hair treatment products oils and facts, amphoteric polymers, humectants, solubilizing agents, emulsifiers, thickeners, germicides, hair tonics, perfumes and the like.

The copolymers in accordance with the invention when they are used in the hair treatment products are preferably such that the hydrophilic monomer (a) is cationic, amphoteric in that it has cationic and anionic natures in its molecule, or amphoteric in that a cationic monomer and an anionic monomer are in admixture. The hydrophilic monomers (a) may be used singly or in combination, but the ratio by weight of the units of a cationic hydrophilic monomer/the units of an anionic or amphoteric hydrophilic monomer which has anionic and cationic natures in its molecule is 1/9 to 9/1.

The copolymers in accordance with the present invention preferably comprises a unit of the hydrophilic monomer (a) in 30 to 99.5% by weight, a unit of the monomer comprising a polysiloxane group (b) in 0.5 to 70% by weight, and a unit of the hydropholic monomer in 0 to 69.5% by weight.

[III] Examples

The present invention is explained more specifically with reference to the following preparation examples and formulation examples without limit thereto. The parts and percentages in the preparation examples are represented by weight. The parts and percentages in the formulation examples are represented by weight on the basis of effective components.

Preparation Example 1

In a five-neck flask equipped with a reflux condenser, a dropping funnel, a thermometer, a glass tube for nitrogen substitution and a stirrer are charged 70 parts of dimethylaminoethyl methacrylate, 25 parts of N-vinylpyrrolidone, 5 parts of polysiloxane FM0721 and 150 parts of anhydrous ethanol. A 0.6 part amount of azobisisobutyronitrile is added to the mixture, and the polymerization is carried out for 8 hours by heating under reflux at 80° C. under a nitrogen stream.

Next, a 50% solution in anhydrous alcohol of propanesultone which is equimolar to the dimethylaminoethyl methacrylate is added dropwise from a dropping funnel into the five-neck flask and heated under reflux at 80° C. for further 6 hours under a nitrogen stream in order to conduct amphoterization reaction. The polymer thus obtained is referred to as "P-i". In an actual practice, the polymer thus obtained had an average molecular weight of 170,000.

Preparation Example 2

In a five-neck flask similar to that in Preparation Example 1 are charged 30 parts of dimethylaminoethyl methacrylate, 70 parts of polysiloxane FM0711 and parts of anhydrous ethanol. One part of azobisisobutyronitrile is added to the mixture, and the polymerization is carried out for 6 hours by heating under reflux at 80° C. under a nitrogen stream.

Next, a 50% solution in anhydrous ethanol of propanesultone which is equimolar to the dimethylaminoethyl methacrylate is added dropwise from a dropping funnel into the five-neck flask and heated under reflux at 80° C. under a nitrogen stream in order to conduct cationization reaction for further 6 hours. The polymer thus obtained is referred to as "P-2". In an actual practice, the polymer obtained had an average molecular weight of 25,000.

Preparation Example 3

In a five-neck flask similar to that in Preparation Example 1 are charged 85 parts of dimethylaminoethyl methacrylate, 11 parts of lauryl methacrylate, 3 parts of polysiloxane FM0725, 1 part of polysiloxane FP-2231 and 67 parts of anhydrous ethanol, and the mixture is heated under reflux at 80° C. under a nitrogen stream. A solution of 0.6 part of azobisisobutyronitrile in 33 parts of ethanol is added to a five-neck flask by dropping from a dropping funnel over a period of 3 hours. Next, 0.3 part of azobisisobutyronitrile was added to the mixture, and the polymerization is carried out for further 6 hours by heating under reflux at 80° C under a nitrogen stream.

Next, a 40% solution in anhydrous ethanol of an aminomethylpropanol neutralization product of monochloracetic acid which is equimolar to the dimethylaminoethyl methacrylate is added dropwise from a dropping funnel into the five-neck flask and heated under reflux at 80° C. for further 6 hours under a nitrogen stream in order to conduct amphoterization reaction.

Then, ethanol is removed by heating while pure water is added by from a dropping funnel to the five-neck flask so as to give an aqueous solution of the polymer. The polymer thus obtained is referred to as "P-3". In an actual practice the polymer obtained had an average molecular weight of 300,000.

Preparation Example 4

In a five-neck flask similar to that in Preparation Example 1 are charged 40 parts of dimethylaminoethyl methacrylate, 35 parts of t-butyl methacrylate, 24 parts of tridecyl methacrylate, 1 part of polysiloxane FM0721 and 150 parts of anhydrous ethanol. 0.6 part of azobisisobutyronitrile is added, and the polymerization is carried out for 8 hours by heating under reflux at 80° C. under a nitrogen stream.

Next, a 40% solution in anhydrous ethanol of a potassium hydroxide neutralization product of monochloracetic acid which is equimolar to the dimethylaminoethyl methacrylate is added dropwise from a dropping funnel into the five-neck flask and heated under reflux at 80° C. for further 12 hours under a nitrogen stream in order to conduct amphoterization reaction.

Suspended materials (potassium chloride) are removed by pressurized filtration from the viscous suspension thus obtained.

The filtrate is passed through a column in which a cation exchange resin ("DIAION PK-220", of which system has been substituted by anhydrous ethanol after regeneration) has been packed and is passed through a column in which an anion exchange resin ("DIAION PA-416" of which system has been substituted by anhydrous ethanol after regeneration) has been packed. The polymer thus obtained is referred to as "P-4". In an actual practice, the polymer obtained had an average molecular weight of 60,000.

Preparation Example 5

In a five-neck flask similar to that in Preparation Example 1 are charged 70 parts of N-vinylpyrrolidone, 30 parts of polysiloxane FM0721 and 100 parts of anhydrous ethanol, and 0.6 part of azobisisobutyronitrile is added to the mixture. The polymerization is carried out for 8 hours by heating under reflux at 80° C. under a nitrogen stream.

The polymer thus obtained is referred to as "P-5". In an actual practice, the polymer obtained had an average molecular weight of 150,000.

Preparation Example 6

In a five-neck flask similar to that in Preparation Example 1 are charged 15 parts of acrylic acid, 5 parts of methacrylic acid, 10 parts of methyl acrylate, 40 parts of butyl methacrylate, 25 parts of lauryl methacrylate, 5 parts of polysiloxane FM0721 and 150 parts of anhydrous ethanol. 0.6 part of benzoyl peroxide is added, and the polymerization is carried out for 6 hours by heating under reflux at 80° C. under a nitrogen stream.

Next, a 50% solution in anhydrous ethanol of triethanolamine which corresponds to 85% molar amount of the acid is added dropwise under .cooling from a dropping funnel into the five-neck flask. The polymer thus obtained is referred to as "P-4". In an actual practice, the polymer obtained had an average molecular weight of 120,000.

Preparation Example 7

In a five-neck flask similar to that in Preparation Example 1 are charged 45 parts of methacrylic acid, 10 parts of methyl methacrylate, 30 parts of iso-butyl methacrylate, 15 parts of palmityl methacrylate and 150 parts of toluene. 0.6 part of benzoyl peroxide is added, and the polymerization is carried out for 6 hours by 35 heating under reflux at 80° C. under a nitrogen stream.

Next, 1 part of benzyltrimethylammonium chloride is added, and 5 parts of polysiloxane FM-0521 is added dropwise from a dropping funnel into the five-neck flask in order to conduct addition reaction by heating under reflux at 80° C. for 6 hours under a nitrogen stream.

Toluene in the toluene solution obtained is removed by evaporation by heating to give a precursor polymer as a solid. The polymer is dissolved in a 5% water-containing ethanol so that it has a concentration of 40%.

Next, a 50% solution in ethanol (containing 5% of water) of aminomethylpropanol which corresponds to 85% molar amount of the residual acid is added dropwise under cooling from a dropping funnel into the five-neck flask. The polymer thus obtained is referred to as "P-7". In an actual practice, the polymer obtained had an average molecular weight of 90,000.

Formulation Example 1

A shampoo composition having the following formulation was prepared.

| | |
|---|---|
| Sodium polyoxyethylenelauryl sulfate (3EO) | 16% |
| Lauroyl diethanolamide | 2% |
| "P-1" | 1.5% |
| Perfume | 0.2% |
| Preservative | 0.1% |
| Coloring matter | trace |
| Pure water | balance |
| | 100% |

When the composition was used for shampoos, hair after washing was combed smoothly, and the hair after drying had an excellent gloss and brilliance and a smooth feeling so that the hair was combed smoothly.

With repeated shampooings, adverse effects such as tackiness were not observed.

Formulation Example 2

A shampoo composition having the formulation was prepared.

| | |
|---|---|
| Sodium polyoxyethylenelauryl sulfate (3EO) | 10% |
| Sodium lauryl sulfate | 8% |
| Lauroyl diethanolamide | 2% |
| "P-3" | 1.5% |
| Pure water | balance |
| | 100% |

When the composition was used for shampoos, excellent effects as in Formulation Example 1 were obtained.

Formulation Example 3

A shampoo composition having the following formulation was prepared.

| | |
|---|---|
| Coconut oil fatty acid dimethylaminosulfobetaine | 10% |
| Sodium polyoxyethylenelauryl sulfate (3EO) | 5% |
| "P-5" | 0.5% |
| Pure water | balance |

-continued

|  | 100% |
|---|---|

When the composition was used for shampoos, excellent effects as in Example 1 was obtained.

Formulation Example 4

A rinse composition having the following formulation was prepared.

| Stearyltrimethylammonium chloride | 1.5% |
|---|---|
| Cetanol | 2% |
| "P-2" | 0.2% |
| Perfume | 0.2% |
| Pure water | balance |
|  | 100% |

When the composition was used for a rinse, hair after rinsing was combed smoothly, and the hair after drying had an excellent gloss and brilliance and a smooth feeling so that the hair was combed smoothly.

With repeated rinsings, adverse effects such as tackiness were not observed.

Formulation Example 5

A hair oil composition having the following formulation was prepared.

| Octamethylcyclotetrasiloxane | 40% |
|---|---|
| "P-2" | 8% |
| Anhydrous ethanol | balance |
|  | 100% |

When the composition was used for a rinse, hair after rinsing was combed smoothly, and the hair after drying had an excellent gloss and brilliance and a smooth feeling so that the hair was combed smoothly. When the hair oil composition was applied to hair and the hair was washed in repeated cycle, adverse effects such as tackiness or development of a feeling of physical disorder due to its accumulation were not observed.

Formulation Example 6

A diluted polymer solution of the following formulation was charged in a spraying can, which were then charged with a liquefied petroleum gas to prepare a hair spray composition.

| A diluted polymer solution | |
|---|---|
| "P-2" | 4 parts |
| Anhydrous ethanol | balance |
|  | 65 parts |
| Liquefied petroleum gas (3 kg/cm² G, 20° C.) | 35 parts |

When the composition was used by spraying it onto hair, it afforded the hair an excellent set maintaining capability as well as an excellent gloss and brilliance and a smooth feeling. When the hair oil composition was applied to the hair was washed in repeated cycle, adverse effects such as tackiness or a feeling of physical disorder due to its accumulation were not observed.

Formulation Example 7

In the same manner as in Formulation Example 6, a hair spray composition was prepared.

| A diluted polymer solution | |
|---|---|
| "P-6" | 3 parts |
| Anhydrous ethanol | balance |
|  | 70 parts |
| Liquefied petroleum gas (3 kg/cm² G, 20° C.) | 30 parts |

When the composition was used by spraying it onto hair, an excellent effect like the Example 6 was obtained.

Formulation Example 8

In the same manner as in Formulation Example 6, a foaming aerosol composition was prepared.

| A diluted polymer solution | |
|---|---|
| "P-4" | 2 parts |
| YUKAFOMER AM-75R 205S* | 2 parts |
| Polyoxyethylene cetyl ether (10EO) | 0.3 parts |
| Polyoxyethylene cetyl ether (2EO) | 0.1 parts |
| Pure water | balance |
|  | 88 parts |
| Liquefied petroleum gas (3 kg/cm² G, 20° C.) | 12 parts |

*"YUKAFOMER AM-75R 205S" is a carboxybetaine type amphoteric polymer which is commercially available from MITSUBISHI PETROCHEMICAL CO., LTD.

When the composition was used by applying it to hair, an excellent effect like the Formulation Example 6 was obtained.

Formulation Example 9

A hair set lotion composition having the following formulation was prepared.

| "P-4" | 3% |
|---|---|
| Pure water | 60% |
| Anhydrous ethanol | balance |
|  | 100% |

When the composition was used by spraying it onto hair, an excellent effect like the Formulation Example 6 was obtained.

What is claimed is:

1. A hair-care product for hair setting with improved combing, gloss and silkiness comprising a polymer dissolved in a solvent selected from the group consisting of water and an alcohol in a concentration of 0.1 to 10% by weight, said polymer having a molecular weight in the range of 1,000 to 500,000 and being a copolymer comprising:

(a) a unit of a hydrophilic ethylenically unsaturated monomer in a quantity of 15 to 59.5% by weight, said monomer being selected from the group consisting of nonionic monomers, anionic monomers, cationic monomers, and amphoteric monomers having an anionic nature and a cationic nature in one molecule, wherein the nonionic monomers are selected from the group consisting of acrylamide and methacrylamide, derivatives of acrylamide and methacrylamide, derivatives of acrylic and methacrylic acid, N-vinylpyrrolidone the anionic monomers are selected from the group consisting of acrylic and methacrylic acid, maleic acid, maleic anhydride, derivatives of acrylic and methacrylic acid and derivatives of acrylamide and methacrylamide, acrylates and methacrylates having a sulfonic acid group, and acrylates and methacrylates having phosphoric acid group; the cationic monomers are selected from the group consisting of derivatives of acrylic and methacrylic acid and derivatives of acrylamide and methacrylamide; and the amphoteric monomers are selected from the group consisting of derivatives of acrylic and methacrylic acid and derivatives of acrylamide and methacrylamide;

(b) a unit of an ethylenically unsaturated monomer having a polysiloxane group, which comprises one or more of the monomers represented by the formula (I)

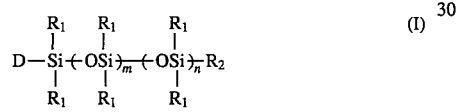

wherein D, $R_1$, $R_2$, m and n have the following meanings, respectively:

D=an unsaturated group having radical polymerizability selected from the group consisting of a vinyl group, a vinylalkylene group, a vinylhydroxyalkylene group, an acryloyloxyalkylene group, methacryloyloxyalkylene group and a (meth)acryloyloxyhydroxyalkylene group formed by reacting (meth)acrylic acid and an epoxy group;

$R_1$=hydrogen atom, a phenyl group, an alkyl group having 1 to 10 carbon atoms, a polyalkylene group, a polyoxyalkylene group of which end has been substituted by an ether or ester group, a polyalkylenepolyamine group, a fatty acid group or a polysiloxane group, respectively;

$R_2$=a hydrogen atom, a phenyl group, an alkyl group having 1 to 10 carbon atoms, a polyalkylene group, a polyoxyalkylene group of which end has been substituted by an ether or ester group, a polyalkylenepolyamine group, a fatty acid group or a polysiloxane group, or an unsaturated group having radical polymerizability selected from the group consisting of a vinyl group, a vinylalkylene group, a vinylhydroxyalkylene group, an acryloyloxalkylene group and a methacryloyloxyalkylene group;

m=an integer from 4 to 150; and n=an integer from 0 to 150, wherein the sum of m and n is within 150, in a quantity of 0.5 to 45% by weight;

(c) a unit of a hydrophobic ethylenically unsaturated monomer in a quantity of 40 to 84.5% by weight, said monomer being selected from the group consisting of alkyl (meth)acrylates having 1 to 24 a carbon atoms in the alkyl, hydrophobic (meth)acrylates and their derivatives selected from the group consisting of butoxyethyl (meth)acrylate, benzyl (meth)acrylate, tetrahydrofurfuryl (meth)acrylate, ethylenglycol di(meth)acrylate, 1,3-butylenglycol di(meth)acrylate, diacetonacrylamide, aromatic unsaturated monomers, and vinyl esters, whereby hair with excellent brilliance and gloss and a smooth feeling can be provided.

2. A hair care product for hair conditioning with improved combing and gloss silkiness comprising a polymer dissolved in a solvent selected from the group consisting of water, an alcohol, and a hydrocarbon of a boiling temperature of 50° to 300° C. in a concentration of 0.1 to 10% by weight, said polymer having a molecular weight in the range of 1,000 to 500,000 and being a copolymer comprising:

(a) a unit of a hydrophilic ethylenically unsaturated monomer in a quantity of 30 to 99.5% by weight, said monomer being selected from the group consisting of nonionic monomers, anionic monomers, cationic monomers, and amphoteric monomers having an anionic nature and a cationic nature in one molecule, wherein the nonionic monomers are selected from the group consisting of acrylamide and methacrylamide, derivatives of acrylamide and methacrylamide, derivatives of acrylic and methacrylic acid, N-vinylpyrrolidone; the anionic monomers are selected from the group consisting of acrylic and methacrylic acid, maleic acid, maleic anhydride, derivatives of acrylic and methacrylic acid and derivatives of acrylamide and methacrylamide, acrylates and methacrylates having a sulfonic acid group, and acrylates and methacrylates having a phosphoric acid group; the cationic monomers are selected from the group consisting of derivatives of acrylic and methacrylic acid and derivatives of acrylamide and methacrylamide; and the amphoteric monomers are selected from the group consisting of derivatives of acrylic and methacrylic acid and derivatives of acrylamide and methacrylamide;

(b) a unit of an ethylenically unsaturated monomer having a polysiloxane group, which comprises one or more of the monomers represented by the formula (I)

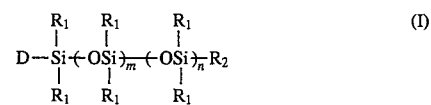

wherein D, $R_1$, $R_2$, m and n have the following meanings, respectively:

D=an unsaturated group having radical polymerizability selected from the group consisting of a vinyl group, a vinylalkylene group, a vinylhydroxyalkylene group, an acryloyloxyalkylene group, methacryloyloxyalkylene group and a (meth)acryloyloxyhydroxyalkylene group formed by reacting (meth)acrylic acid and an epoxy group;

$R_1$=a hydrogen atom, a phenyl group, an alkyl group having 1 to 10 carbon atoms, a polyalkylene group, a polyoxyalkylene group of which end has been substituted by an ether or ester group, a polyalkylenepolyamine group, a fatty acid group or a polysiloxane group, respectively;

$R_2$=a hydrogen atom, a phenyl group, an alkyl group having 1 to 10 carbon atoms, a polyalkylene group, a polyoxyalkylene group of which end has been substituted by an ether or ester group, a polyalkylenepolyamine group, a fatty acid group or a polysiloxane group, or an unsaturated group having radical polymerizability selected from the group consisting of a vinyl group, a vinylalkylene group, a vinylhydroxyalkylene group, an acryloyloxalkylene group and a methacryloyloxyalkylene group;

m=an integer from 4 to 150; and n=an integer from 0 to 150, wherein the sum of m and n is within 150, in a quantity of 0.5 to 70% by weight;

(c) a unit of a hydrophobic ethylenically unsaturated monomer in a quantity of 0 to 69.5% by weight, said monomer being selected from the group consisting of alkyl (meth)acrylates having 1 to 24 carbon atoms in the alkyl, hydrophobic (meth)acrylates and their derivatives selected from the group consisting of butoxyethyl (meth)acrylate, benzyl (meth)acrylate, tetrahydrofurfuryl (meth)acrylate, ethylenglycol di(meth)acrylate, 1,3-butylenglycol di(meth)acrylate, diacetonacrylamide, aromatic unsaturated monomers, and vinyl esters, whereby hair with excellent brilliance and gloss and a smooth feeling can be provided.

3. The hair-care product for hair setting or hair conditioning according to claim 1, wherein the ethylenically unsaturated monomer having a polysiloxane group (b) comprises one or a mixture of the two or more of the monomers represented by the formula (II) to (IV) which fall within the scope of the monomer of the formula (I):

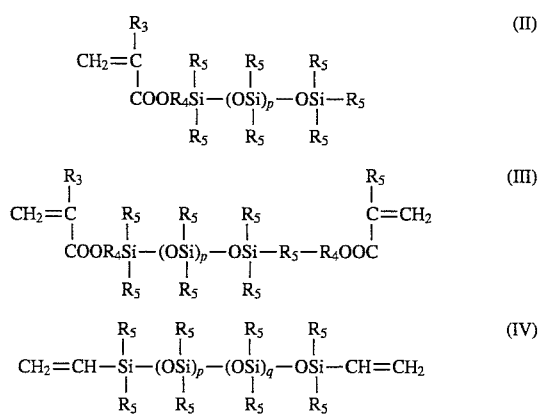

wherein $R_3$ to $R_5$ and p and q have the following meanings independently of each other between the formulae:

$R_3$=a hydrogen atom or a methyl group;

$R_4$=an alkylene group having 1 to 4 carbon atoms;

$R_5$=an alkyl group having 1 to 10 carbon atoms or a phenyl group;

p=an integer of 1 or more; and q=an integer of 1 or more, wherein the sum of p and q are within 150.

4. The hair-care product for hair setting according to claim 1, wherein the copolymer comprises monomer (a) units, in a quantity of 20 to 59.5% by weight; monomer (b) units in a quantity of 0.5 to 40% by weight; and monomer (c) units in quantity of 40 to 79.5% by weight.

5. The hair-care product for hair setting according to claim 1, wherein the copolymer comprises (a) unit of a hydrophilic unsaturated monomer which is a mixture of a cationic unsaturated monomer and an anionic unsaturated monomer, the weight ratio of the canionic monomer to the anionic monomer being 1/9 to 9/1, in a quantity of 20 to 59.5% by weight; (b) a unit of an unsaturated monomer having a polysiloxane group in a quantity of 0.5 to 40% by weight; and monomer units (c) in a quantity of 40 to 79.5% by weight.

6. The hair-care product for hair setting according to claim 1, wherein the copolymer comprising monomer (a) units of a hydrophilic unsaturated monomer which is a cationic unsaturated monomer in a quantity of 15 to 54.5% by weight; monomer units (b) in a quantity of 0.5 to 45% by weight; and monomer (c) units in a quantity of 40 to 84.5% by weight.

7. The hair-care product for hair conditioning according to claim 2, wherein the monomer (a) comprises a unit of a hydrophilic unsaturated monomer which is a combination of a cationic monomer and an anionic monomer or a combination of a cationic monomer and an amphoteric unsaturated monomer which has an anionic nature and a cationic nature in its molecule, the weight ratio of the cationic monomer to the anionic monomer or cationic monomer to the amphoteric monomer is 1/9 to 9/1.

* * * * *

UNITED STATES PATENT AND TRADEMARK OFFICE
CERTIFICATE OF CORRECTION

PATENT NO. : 5,480,634
DATED : January 2, 1996
INVENTOR(S) : Kazuhide Hayama, et al.

It is certified that error appears in the above-indentified patent and that said Letters Patent is hereby corrected as shown below:

TITLE PAGE:
Item [22] Filed: Change "Dec. 2, 1993" to --Dec. 20, 1993--

Signed and Sealed this

Nineteenth Day of March, 1996

Attest:

BRUCE LEHMAN

*Attesting Officer*      *Commissioner of Patents and Trademarks*